United States Patent [19]

Hillman et al.

[11] Patent Number: 5,854,023

[45] Date of Patent: Dec. 29, 1998

[54] POLYNUCLEOTIDES ENCODING HUMAN S-ADENOSYL-5-HOMOCYSTEINE HYDROLASE DERIVED FROM BLADDER

[75] Inventors: Jennifer L. Hillman; Neil C. Corley, both of Mountain View; Preeti Lal, Santa Clara; Purvi Shah, Sunnyvale, all of Calif.

[73] Assignee: Incyte Pharmaceuticals, Inc., Palo Alto, Calif.

[21] Appl. No.: 896,005

[22] Filed: Jul. 17, 1997

[51] Int. Cl.[6] .............................. C12P 21/06; C12N 9/14; C12N 5/00; C07H 17/00

[52] U.S. Cl. ...................... 435/69.1; 435/195; 435/320.1; 435/252.3; 435/325; 536/23.2

[58] Field of Search ................................ 435/69.1, 183, 435/195, 320.1, 252.3, 325; 536/23.2

[56] References Cited

PUBLICATIONS

Goldberg, D.M. and Diamandis, E.P., "Models of Neoplasia and Their Diagnostic Implications: A Historical Perspective" *Clin.Chem.* (1993) 39:2360–2374.

Gloria, L. et al., "DNA Hypomethylation and Proliferative Activity are Increased in the Rectal Mucosa of Patients with Long–Standing Ulcerative Colitis" *Cancer* (1996) 78:2300–2306.

Turker, M.S. and Bestor, T.H., "Formation of methylation patterns in the mammalian genome" *Mutat.Res.* (1997) 386:119–130.

Stryer, L., *Biochemistry*, W.H. Freeman and Company, San Francisco, CA (1981) p. 612.

Willis, D.B. et al., "Transcription of Methylated Viral DNA by Eukaryotic RNA Polymerase II" *Cell Biophys.* (1989) 15:97–111.

Bottiglieri, T. And Hyland, K., "S–adenosylmethionine levels in psychiatric and neurological disorders: a review" *Acta Neurol.Scand.Suppl.* (1994) 154:19–26.

Montgomery, J.A. et al., "Carbocyclic Analogue of 3–Deazaadenosine: A Novel Antiviral Agent Using S–Adenosylhomocysteine Hydrolase as a Pharmacological Target" *J.Med.Chem.* (1982) 25:626–629.

Newsholme, E.A. and Leech, A.R., *Biochemistry for the Medical Sciences*, John Wiley & Sons (1983), p. 436.

Palmer, J.L. and Abeles, R.H., "The Mechanism of Action of S–Adenosylhomocysteinase" *J.Biol.Chem.* (1979) 254:1217–1226.

Coulter–Karis, D.E. and Hershfield, M.S., "Sequence of full length cDNA for human S–adenosylhomocysteine hydrolase" *Ann.Hum.Genet.* (1989) 53:169–175. (GI 178276; GI 178277).

Bethin, K.E. et al., "Identification of a Major Hepatic Copper Binding Protein as S–Adenosylhomocysteine Hydrolase" *J.Biol.Chem.* (1995) 270:20698–20702. (GI 904131; GI 904132).

Martin, C.H. et al., "Complete sequence of the bithorax complex of *Drosophila*" *Proc.Natl.Acad.Sci.USA* (1995) 92:8398–8402. (GI 969077; GI 969078).

DeLorenzi, M. et al., "Evidence that the abdominal–B r element function is conferred by a trans–regulatory homeoprotein" *EMBO J.* (1988) 7:3223–3231.

Inagaki, H. et al., "A Large DNA–binding Nuclear Protein with RNA Recognition Motif and Serine/Arginine–rich Domain" *J.Biol.Chem.* (1996) 271:12525–12531.

Harada, Y. et al., "Complementary DNA Sequence and Chromosomal Localization of xpg, the Mouse Counterpart of Human Repair Gene XPG/ERCC5" *Genomics* (1995) 28:59–65.

Wnuk, S.F. et al., "Nucleic Acid Related Compounds. 84. Synthesis of 6'–(E and Z)–Halohomovinyl Derivatives of Adenosine, Inactivation of S–adenosyl–L–homocysteine Hydrolase, and Correlation of Anticancer and Antiviral Potencies with Enzyme Inhibition" *J.Med.Chem.* (1994) 37:3579–3587.

Phadtare, S. et al., "Unsaturated and Carbocyclic Nucleoside Analogues: Synthesis, Antitumor, and Antiviral Activity." *J.Med.Chem.* (1991) 34:421–429.

Warzocha, K. "2–Chlorodeoxyadenosine Inhibits Activity of Adenosine Deaminase and S–Adenosylhomocysteine Hydrolase in Patients With Chronic Lymphocytic Leukemia" *Eur.J.Cancer* (1997) 33:170–173.

Coulter–Karis, D.E. and Hershfield, M.S. (GI 178276), GenBank Sequence Database (Accession M61831), National Center for Biotechnology Information, National Library of Medicine, Bethesda, Maryland, 20894. (GI 178277).

Martin, C.H. et al. (GI 969077), GenBank Sequence Database (Accession U31961), National Center for Biotechnology Information, National Library of Medicine, Bethesda, Maryland, 20894.

Petrovic, N. et al., (GI 904131), GenBank Sequence Database (Accession L32836), National Center for Biotechnology Information, National Library of Medicine, Bethesda, Maryland, 20894. (GI 904132).

Hohman, R.J. et al., "Purification of S–Adenosyl–L–homocysteine hydrolase from *Dictyostelium discoideum*: Reversible Inactivation by cAMP and 2'–Deoxyadenosine" *Arch.Biochem.Biophy.* (1984) 233:785–795.

Hohman, R.J. and Veron, M., "S–Adenosyl–L–homocysteine hydrolase from *Dictyostelium discoideum* is inactivated by cAMP and reactivated by NAD" *FEBS Lett.* (1984) 165:265–268. (GI 969077; GI 969078).

Primary Examiner—Karen Cochrane Carlson
Attorney, Agent, or Firm—Incyte Pharmaceuticals, Inc.

[57] ABSTRACT

The invention provides a human S-adenosyl-5-homocysteine hydrolase (SAHH) and polynucleotides which identify and encode SAHH. The invention also provides expression vectors, host cells, agonists, antibodies and antagonists. The invention also provides methods for treating disorders associated with expression of SAHH.

10 Claims, 14 Drawing Sheets

```
                        9          18          27          36          45          54
5'  C   AGG GAG GAG    CTG AAG CAG    GCC AAG GAG    ATC GAG GAC    GCC GAG AAG    TAC TCC 63          72          81          90          99         108
    TTC ATG GCC ACC    GTC ACC AAG    GCG CCC AAG    AAG CAA ATC    CAG TTT GCT    GAT GAC
         M   A   T      V   T   K      A   P   K      K   Q   I      Q   F   A      D   D 117         126         135         144         153         162
    ATG CAG GAG TTC    ACC AAA TTC    CCC ACC AAA    ACT GGC CGA    AGA TCT TTG    TCT CGC
     M   Q   E   F      T   K   F      P   T   K      T   G   R      R   S   L      S   R 171         180         189         198         207         216
    TCG ATC TCA CAG    TCC ACT GAC    AGC TAC AGT    GCT GCA TCC    TAC ACA GAT
     S   I   S   Q      S   T   D      S   Y   S      A   A   S      Y   T   D 225         234         243         252         261         270
    AGC TCT GAT GAT    GAG GTT TCT    CCC CGA GAG    AAG CAG CAA    ACC AAC TCC    AAG GGC
     S   S   D   D      E   V   S      P   R   E      K   Q   Q      T   N   S      K   G 279         288         297         306         315         324
    AGC AGC AAT TTC    TGT GTG AAG    AAC ATC AAG    CAG GCA GAA    TTT GGA CGC    CGG GAG
     S   S   N   F      C   V   K      N   I   K      Q   A   E      F   G   R      R   E 333         342         351         360         369         378
    ATT GAG ATT GCA    GAG CAA GAC    ATG TCT GCT    CTG ATT TCA    CTC AGG AAA    CGT GCT
     I   E   I   A      E   Q   D      M   S   A      L   I   S      L   R   K      R   A
```

FIGURE 1A

| | | | | | | | | |
|---|---|---|---|---|---|---|---|---|
| | 387 | 396 | 405 | 414 | 423 | 432 | | |
| CAG | GGG | GAG | AAG | CCC | TTG | GCT | GGT | GCT AAA ATA GTG GGC TGT ACA CAC ATC ACA |
| Q | G | E | K | P | L | A | G | A K I V G C T H I T |
| | 441 | 450 | 459 | 468 | 477 | 486 | | |
| GCC | CAG | ACA | GCG | GTG | TTG | ATT | GAG | ACA CTC TGT GCC CTG GGG GCT CAG TGC CGC |
| A | Q | T | A | V | L | I | E | T L C A L G A Q C R |
| | 495 | 504 | 513 | 522 | 531 | 540 | | |
| TGG | TCT | GCT | TGT | AAC | ATC | TAC | TCA | ACT CAG AAT GAA GTA GCT GCA GCA CTG GCT |
| W | S | A | C | N | I | Y | S | T Q N E V A A A L A |
| | 549 | 558 | 567 | 576 | 585 | 594 | | |
| GAG | GCT | GGA | GTT | GCA | GTG | TTC | GCT | TGG AAG GGC TCA GAG TCA GAA GAT GAC TTC TGG |
| E | A | G | V | A | V | F | A | W K G S E S E D D F W |
| | 603 | 612 | 621 | 630 | 639 | 648 | | |
| TGG | TGT | ATT | GAC | CGC | TGT | GTG | AAC | ATG GAT GGG TGG CAG GCC AAC ATG ATC CTG |
| W | C | I | D | R | C | V | N | M D G W Q A N M I L |
| | 657 | 666 | 675 | 684 | 693 | 702 | | |
| GAT | GAT | GGG | GGA | GAC | TTA | ACC | CAC | TGG GTT TGT AAG TAT CCA AAC GTG TTT |
| D | D | G | G | D | L | T | H | W V C K Y P N V F |
| | 711 | 720 | 729 | 738 | 747 | 756 | | |
| AAG | AAG | ATC | CGA | GGC | ATT | GTG | GAA | GAG AGC GTG ACT GGT GTT CAC AGG CTG TAT |
| K | K | I | R | G | I | V | E | E S V T G V H R L Y |

FIGURE 1B

```
       765             774             783             792             801             810
CAG CTC TCC AAA GCT GGG AAG CTC TGT GTT CCG GCC ATG AAC GTC AAT GAT TCT
 Q   L   S   K   A   G   K   L   C   V   P   A   M   N   V   N   D   S 819             828             837             846             855             864
GTT ACC AAA CAG AAG TTT GAT AAC TTG TAC TGC TGC CGA GAA TCC ATT TTG GAT
 V   T   K   Q   K   F   D   N   L   Y   C   C   R   E   S   I   L   D 873             882             891             900             909             918
GGC CTG AAG AGG ACC ACA GAT GTG ATG TTT GGT GGG AAA CAA GTG GTG GTG TGT
 G   L   K   R   T   T   D   V   M   F   G   G   K   Q   V   V   V   C 927             936             945             954             963             972
GGC TAT GGT GAG GTA ACC AAG GGC TGC TGT GCT CTC AAA GCT CTT GGA GTG GCA
 G   Y   G   E   V   T   K   G   C   C   A   L   K   A   L   G   V   A 981             990             999            1008            1017            1026
ATT GTC TAC ATT ACC GAA ATC GAC CCC ATC TGT CTG CAG CGG CAA GTC GAT GAT
 I   V   Y   I   T   E   I   D   P   I   C   L   Q   R   Q   V   D   D 1035            1044            1053            1062            1071            1080
GGG TTC AGG GTG GTA AAG CTA AAT GAA GTC ATC CGG CAA GTC GAT GTC GTA ATA
 G   F   R   V   V   K   L   N   E   V   I   R   Q   V   D   V   V   I 1089            1098            1107            1116            1125            1134
ACT TGC ACA GGA AAT GTA AAG AAT GTA ACA CGG GAG CAC TTG GAT CGC ATG AAA
 T   C   T   G   N   V   K   N   V   T   R   E   H   L   D   R   M   K
```

FIGURE 1C

```
                    1143            1152            1161            1170            1179            1188
AAC AGT TGT ATC GTA TGC AAT ATG GGC CAC TCC AAC ACA GAA ATC GAT GTG ACC
 N   S   C   I   V   C   N   M   G   H   S   N   T   E   I   D   V   T 1197            1206            1215            1224            1233            1242
AGC CTC CGC ACT CCG GAG CTG ACG TGG GAG CGA GTA CGT TCT CAG GTG GAC CAT
 S   L   R   T   P   E   L   T   W   E   R   V   R   S   Q   V   D   H 1251            1260            1269            1278            1287            1296
GTC ATC TGG CCA GAT GGC AAA CGA GTT GTC CTC CTG GCA GAG GGT CGT CTA CTC
 V   I   W   P   D   G   K   R   V   V   L   L   A   E   G   R   L   L 1305            1314            1323            1332            1341            1350
AAT TTG AGC TGC TCC ACA GTT CCC ACC TTT GTT CTG TCC ATC ACA GCC ACA ACA
 N   L   S   C   S   T   V   P   T   F   V   L   S   I   T   A   T   T 1359            1368            1377            1386            1395            1404
CAG GCT TTG GCA CTG ATA GAA CTC TAT AAT GCA CCC GAG GGG CGA TAC AAG CAG
 Q   A   L   A   L   I   E   L   Y   N   A   P   E   G   R   Y   K   Q 1413            1422            1431            1440            1449            1458
GAT GTG TAC TTG CTT CCT AAG AAA ATG GAT GAA TAC GTT GCC AGC TTG CAT CTG
 D   V   Y   L   L   P   K   K   M   D   E   Y   V   A   S   L   H   L 1467            1476            1485            1494            1503            1512
CCA TCA TTT GAT GCC CAC CTT ACA GAG CTG ACA GAT GAC CAA GCA AAA TAT CTG
 P   S   F   D   A   H   L   T   E   L   T   D   D   Q   A   K   Y   L

FIGURE 1D
```

```
       1521        1530        1539        1548        1557        1566
GGA CTC AAC AAA AAT GGG CCA TTC AAA CCT AAT TAT TAC AGA TAC TAA TGG ACC
 G   L   N   K   N   G   P   F   K   P   N   Y   Y   R   Y 1575        1584        1593        1602        1611        1620
ATA CTA CCA AGC ATT CAA TCG GGA TGC TTT GGG CCA TGC TGC CAG TCC ACC TGA 1629        1638        1647        1656        1665        1674
ACC ACA CAC TCT AAA GAA ATA TTT AAG ATA ACT TTT ATT TTC TTC TTA CTC 1683        1692        1701        1710        1719        1728
CTT TCC TCT TGA TTT TTT TCC TAT AAT TTC ATT CTT GTT TTT TCA TCT CAT TAT 1737        1746        1755        1764        1773        1782
CCA AGT TCT GCA GAC CAC ACA GGA ACT TGC TTC ATG GCT CTT TAG ATG AAA TAG 1791        1800        1809        1818        1827        1836
AAG TTC AGG GTT CCT CAC TCT AGT CAC TAA AGA AGG ATT TTA CTC TCC CAG CCC 1845        1854        1863        1872        1881        1890
AGA AAG GTG ATT CTT TCT TTA CCA TTT CTG GGG ACT TTA GTC TTA ATT AGG TAC 1899        1908        1917        1926        1935        1944
CTT ATT AAC AGG AAA TGC TAA GGT ACC TTC TCT GTG GAA TAA TCT GCA ATG TCT 1953        1962        1971        1980        1989        1998
AAA TCG CCT TAA AAG AGC CCA TTT CTT AGC TGC TGA AAT CAG TGC TCT TTC ACT
```

FIGURE 1E

```
       2007       2016       2025       2034       2043       2052
TCT TCA GAG AAG CAG GGA TGG TAC CTA CCC GGC AGG TAG GTT AGA TGT GGG TGG
       2061       2070       2079       2088       2097       2106
TGC ATG TTA ATT TCC CTT AGA AGT TCC AAG CCC TGT TTC CTG CGT AAA GGT GGT
       2115       2124       2133       2142       2151       2160
ATG TCC AGT TCA GAG ATG TGT ATA ATG AGC ATG TGT TAA GAT CAG GAG GCC
       2169       2178       2187       2196       2205       2214
CAC TTG GAT TTA TAG TAT AGC CCT TCC TCC ACT CCC ACC AGA CTT GCT CAT TTT
       2223       2232       2241       2250       2259       2268
TCG AGT TTT TAA CTA GAC TAC ACT CTA TTG AGT TTA ATT TTG TCC TCT AGG ATT
       2277       2286       2295       2304       2313       2322
TAT TTC TGT TGT CCA AAA AAA AAA AAG AAA AGA AAA ATT AAG GAG AAT TTT
       2331       2340       2349       2358       2367       2376
TGG TGT TAA TGC TGA GGA ATT GCT TGA GTG GTT AGT TGT TAC CAA TTT CTC TTT
       2385       2394       2403       2412       2421       2430
TGA ACC TTT GGA GCT AAG GAT GCT GAG TCT AGA GAA ATG CTA GTC TCA AGC CCT
       2439       2448       2457       2466       2475       2484
GTT AAG TCC CTC TGT TTC TAG CCC GTA GTT CAT AGC ATC AGT GAA CTG GAG CCA
```

FIGURE 1F

```
     2493            2502             2511             2520             2529             2538
CAA CAG CAA ATT CTA TCA GCT GTG TAC CAT ACA GCT TGT GCT GAA GGC GAA TTT 2547            2556             2565             2574             2583             2592
CTT GAG CCA TTA CTC AGT ATA AAG CAC TGA GTT CTA TCT TTA GGA TTT ATC TTT 2601            2610             2619             2628             2637             2646
AAG AGC AAA TTT CTG GTC AGC TGT GCT TCT GCA ACC TAA AAT ATT TAA AGG GAG 2655            2664             2673             2682             2691             2700
GTA GGT GTG GGC AGG AGG AGG AAT GAT AAA TTG GGC CAG GGC AAG AAA AAT CTA 2709            2718             2727             2736             2745             2754
GCT TCA TAT AAT TTG TCT GGG ACT ATA CAC CCT ATA TAA TGT TAG TTT TAC AGA 2763            2772             2781             2790             2799             2808
AGT AAT ATG ACT TTT GAT TGC TAC ATA CCA CAA AGA GTT TAT GAA CTG AGA TCA 2817            2826             2835             2844             2853             2862
TAA AGG GCA ACT GAT GTG TGA AGA AAG TAG TCA GTA CAT CCT GGC TCA TGC TCT 2871            2880             2889             2898             2907             2916
GAA AGA ATA TCC AGA GAG GCT CTC TCA AAG ATC AGG GAG ATG TAT TCC CAT GCC 2925            2934             2943             2952             2961             2970
ATG CAC CCT GCT TCC CAG CAT TTC TGC ATG GTC AAG TGA GCT TTA TGC TCA TGA
```

FIGURE 1G

```
           2979        2988        2997        3006        3015        3024
GCT TTA AGT ATA TAA TTA TCC AGG ATT TTA AAT CCT CAA CTT GTT CTA GCT TGT
     3033        3042        3051        3060        3069        3078
GAT CCC TCA AAG TTG GGT CAT ACG TTA GTG CTA GAT ACT AGA AAT TTT CAC TTT
     3087        3096        3105        3114        3123        3132
TCC ACT GAT CAG AGA GAC AGA CAT TAA AAA CAA AAA TAG AAG AAA GGA AAG CTT
     3141        3150        3159        3168        3177        3186
TCA CCC TGC AGC TTC TTA GCA GGG AAC AAT TGT CTT GCC AAA ACT TTT TTT CCC
     3195        3204        3213        3222        3231        3240
TTT TCT CTC CCA TTT TCT TTT ACC CAA TCC CTT ACT CCT TGC CAG TGT GAC
     3249        3258        3267        3276        3285        3294
CAT GCT TTC TTC TCT GTA GAT GTT AAC AGT TAA GGC CTA TTT TCC TCG GGC ACT
     3303        3312        3321        3330        3339        3348
TAA CCA ACC AAT CAG AAC ACC ACA TCT GTT AGG GGA GGT AAC CTG GCC AAC AGT
     3357        3366        3375        3384        3393        3402
GTA TCC ATC ACG TTA GCC CTG CTG GAG GGA AGG GAC CCA CAT TCA CCT GCC CTC
     3411        3420        3429        3438        3447        3456
TGA CCT GCC CCT TGA TCC CAT ATC TAT TAC CGT GTC CAT AGG AAT AAT AGG TAA
```

FIGURE 1H

```
            3465      3474      3483      3492      3501      3510
        GGG CTC TGT CTC TGT CAA GCC ATG TAA CAA AGG ACA CTG TTA AAA AAA AAA
            3519      3528      3537      3546      3555      3564
        AGT CTG GCA TCA GAG GGA GCA TGT GGA GAG CAA CTT GGG AAG AAC AAG TTC ATT
            3573      3582      3591      3600      3609      3618
        TTG TAT TGA ATG ATT TTT AAT GAA TGC AAT ATT AAT CCT TGC AGA TGA GCA ATA
            3627      3636      3645      3654      3663      3672
        ATC ATT AAA ATC GAT TAA AAT GAT AAG ACC TTA AAA AAA AAA AAA AAA AAA 3'
```

| | | |
|---|---|---|
| 280 | G G K Q V V V C G Y G E V G K G C C A A | 1519044 |
| 273 | G G K Q V V I C G Y G D V G K G C A Q S | GI 969078 |
| 212 | A G K V A V V A G Y G D V G K G C A Q A | GI 178277 |
| 212 | A G K V A V V A G Y G D V G K G C A Q A | GI 904132 |
| 300 | L K A L G A I V Y I T E I D P I C A L Q | 1519044 |
| 293 | L K G Q G C I V Y V T E V D P I C A L Q | GI 969078 |
| 232 | L R G F G A R V I I T E I D P I N A L Q | GI 178277 |
| 232 | L R G F G A R V I I T E I D P I N A L Q | GI 904132 |
| 320 | A C M D G F R V V K L N E V I R Q V D V | 1519044 |
| 313 | A A M D G F R V V R L N E V I R T V D V | GI 969078 |
| 252 | A A M E G Y E V T T M D E A C Q E G N I | GI 178277 |
| 252 | A A M E G Y E V T T M D E A C K E G N I | GI 904132 |
| 340 | V I T C T G N K N V V T R E H L D R M K | 1519044 |
| 333 | V V T A T G N K N V I T R D H M N R M K | GI 969078 |
| 272 | F V T T T G C I D I I L G R H F E Q M K | GI 178277 |
| 272 | F V T T T G C V D I I L G R H F E Q M K | GI 904132 |
| 360 | N S C I V C N M G H S N T E I D V T S L | 1519044 |
| 353 | N G C I L C N M G H S C S E I D V N G L | GI 969078 |
| 292 | D D A I V C N I G H F D V E I D V K W L | GI 178277 |
| 292 | D D A I V C N I G H F D V E I D V K W L | GI 904132 |
| 380 | R T P E L T W E R V R S Q V D H V I W P | 1519044 |
| 373 | H T P E L T W E R V R S Q V D H I R W P | GI 969078 |
| 312 | N E N A V E K V N I K P Q V D R Y R L K | GI 178277 |
| 312 | N E N A V E K V N I K P Q V D R Y W L K | GI 904132 |
| 400 | D G K R V V L L A E G R L L N L S C S - | 1519044 |
| 393 | D G R M I I L L A E G R L V N L S C S - | GI 969078 |
| 332 | N G R R I I L L A E G R L V N L G C A M | GI 178277 |
| 332 | N G R R I I L L A E G R L V N L G C A M | GI 904132 |

FIGURE 2D

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
(A) LENGTH: 500 amino acids
(B) TYPE: amino acid
(C) STRANDEDNESS: single
(D) TOPOLOGY: linear (vii) IMMEDIATE SOURCE:
(A) LIBRARY: BLADTUT04
(B) CLONE: 1519044

(xi) SEQUENCE DESCRIPTION: SEQ ID NO:1:

```
Met Ala Thr Val Thr Lys Ala Pro Lys Lys Gln Ile Gln Phe Ala Asp
  1               5                  10                  15

Asp Met Gln Glu Phe Thr Lys Phe Pro Thr Lys Thr Gly Arg Arg Ser
                 20                  25                  30

Leu Ser Arg Ser Ile Ser Gln Ser Ser Thr Asp Ser Tyr Ser Ser Ala
             35                  40                  45

Ala Ser Tyr Thr Asp Ser Ser Asp Asp Glu Val Ser Pro Arg Glu Lys
         50                  55                  60

Gln Gln Thr Asn Ser Lys Gly Ser Ser Asn Phe Cys Val Lys Asn Ile
 65                  70                  75                  80

Lys Gln Ala Glu Phe Gly Arg Arg Glu Ile Glu Ile Ala Glu Gln Asp
                 85                  90                  95

Met Ser Ala Leu Ile Ser Leu Arg Lys Arg Ala Gln Gly Glu Lys Pro
                100                 105                 110

Leu Ala Gly Ala Lys Ile Val Gly Cys Thr His Ile Thr Ala Gln Thr
            115                 120                 125

Ala Val Leu Ile Glu Thr Leu Cys Ala Leu Gly Ala Gln Cys Arg Trp
        130                 135                 140

Ser Ala Cys Asn Ile Tyr Ser Thr Gln Asn Glu Val Ala Ala Ala Leu
145                 150                 155                 160

Ala Glu Ala Gly Val Ala Val Phe Ala Trp Lys Gly Glu Ser Glu Asp
                165                 170                 175

Asp Phe Trp Trp Cys Ile Asp Arg Cys Val Asn Met Asp Gly Trp Gln
                180                 185                 190

Ala Asn Met Ile Leu Asp Asp Gly Gly Asp Leu Thr His Trp Val Cys
            195                 200                 205

Lys Lys Tyr Pro Asn Val Phe Lys Lys Ile Arg Gly Ile Val Glu Glu
210                 215                 220

Ser Val Thr Gly Val His Arg Leu Tyr Gln Leu Ser Lys Ala Gly Lys
225                 230                 235                 240

Leu Cys Val Pro Ala Met Asn Val Asn Asp Ser Val Thr Lys Gln Lys
                245                 250                 255

Phe Asp Asn Leu Tyr Cys Cys Arg Glu Ser Ile Leu Asp Gly Leu Lys
            260                 265                 270

Arg Thr Thr Asp Val Met Phe Gly Gly Lys Gln Val Val Val Cys Gly
        275                 280                 285

Tyr Gly Glu Val Gly Lys Gly Cys Cys Ala Ala Leu Lys Ala Leu Gly
        290                 295                 300
```

| | | | | | | | | | | | | | | | |
|---|---|---|---|---|---|---|---|---|---|---|---|---|---|---|---|
| Ala | Ile | Val | Tyr | Ile | Thr | Glu | Ile | Asp | Pro | Ile | Cys | Ala | Leu | Gln | Ala |
| 305 | | | | 310 | | | | | 315 | | | | | | 320 |
| Cys | Met | Asp | Gly | Phe | Arg | Val | Val | Lys | Leu | Asn | Glu | Val | Ile | Arg | Gln |
| | | | | 325 | | | | 330 | | | | | 335 | | |
| Val | Asp | Val | Val | Ile | Thr | Cys | Thr | Gly | Asn | Lys | Asn | Val | Val | Thr | Arg |
| | | | 340 | | | | | 345 | | | | | 350 | | |
| Glu | His | Leu | Asp | Arg | Met | Lys | Asn | Ser | Cys | Ile | Val | Cys | Asn | Met | Gly |
| | | 355 | | | | | 360 | | | | | 365 | | | |
| His | Ser | Asn | Thr | Glu | Ile | Asp | Val | Thr | Ser | Leu | Arg | Thr | Pro | Glu | Leu |
| | | 370 | | | | 375 | | | | | 380 | | | | |
| Thr | Trp | Glu | Arg | Val | Arg | Ser | Gln | Val | Asp | His | Val | Ile | Trp | Pro | Asp |
| 385 | | | | | 390 | | | | | 395 | | | | | 400 |
| Gly | Lys | Arg | Val | Val | Leu | Leu | Ala | Glu | Gly | Arg | Leu | Leu | Asn | Leu | Ser |
| | | | | 405 | | | | | 410 | | | | | 415 | |
| Cys | Ser | Thr | Val | Pro | Thr | Phe | Val | Leu | Ser | Ile | Thr | Ala | Thr | Thr | Gln |
| | | | 420 | | | | | 425 | | | | | 430 | | |
| Ala | Leu | Ala | Leu | Ile | Glu | Leu | Tyr | Asn | Ala | Pro | Glu | Gly | Arg | Tyr | Lys |
| | | | 435 | | | | | 440 | | | | | 445 | | |
| Gln | Asp | Val | Tyr | Leu | Leu | Pro | Lys | Lys | Met | Asp | Glu | Tyr | Val | Ala | Ser |
| | | 450 | | | | | 455 | | | | | 460 | | | |
| Leu | His | Leu | Pro | Ser | Phe | Asp | Ala | His | Leu | Thr | Glu | Leu | Thr | Asp | Asp |
| 465 | | | | | 470 | | | | | 475 | | | | | 480 |
| Gln | Ala | Lys | Tyr | Leu | Gly | Leu | Asn | Lys | Asn | Gly | Pro | Phe | Lys | Pro | Asn |
| | | | | 485 | | | | | 490 | | | | | 495 | |
| Tyr | Tyr | Arg | Tyr | | | | | | | | | | | | |
| | | | 500 | | | | | | | | | | | | |

( 2 ) INFORMATION FOR SEQ ID NO:2:

( i ) SEQUENCE CHARACTERISTICS:
        ( A ) LENGTH: 2226 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: BLADTUT04
        ( B ) CLONE: 1519044

( x i ) SEQUENCE DESCRIPTION: SEQ ID NO:2:

```
GTTGCCAGCT TGCATCTGCC ATCATTTGAT GCCCACCTTA CAGAGCTGAC AGATGACCAA      60

GCAAAATATC TGGGACTCAA CAAAAATGGG CCATTCAAAC CTAATTATTA CAGATACTAA     120

TGGACCATAC TACCAAGGAC CAGTCCACCT GAACCACACA CTCTAAAGAA ATATTTTTA     180

AGATAACTTT TATTTTCTTC TTACTCCTTT CCTCTTGATT TTTTTCCTAT AATTTCATTC     240

TTGTTTTTTC ATCTCATTAT CCAAGTTCTG CAGACCACAC AGGAACTTGC TTCATGGCTC     300

TTTAGATGAA ATAGAAGTTC AGGGTTCCTC ACTCTAGTCA CTAAAGAAGG ATTTTACTCT     360

CCCAGCCCAG AAAGGTGATT CTTTCTTTAC CATTTCTGGG GACTTTAGTC TTAATTAGGT     420

ACCTTATTAA CAGGAAATGC TAAGGTACCT TCTCTGTGGA ACAATCTGCA ATGTCTAAAT     480

CGCCTTAAAA GAGCCCATTT CTTAGCTGCT GAAATCAGTG CTCTTTCACT TCTTCAGAGA     540

AGCAGGGATG GTACCTACCC GGCAGGTAGG TTAGATGTGG GTGGTGCATG TTAATTTCCC     600

TTAGAAGTTC CAAGCCCTGT TTCCTGCGTA AAGGTGGTAT GTCCAGTTCA GAGATGTGTA     660

TAATGAGCAT GGCTTGTTAA GATCAGGAGG CCCACTTGGA TTTATAGTAT AGCCCTTCCT     720

CCACTCCCAC CAGACTTGCT CATTTTTCGA GTTTTAACT AGACTACACT CTATTGAGTT     780
```

-continued

```
TAATTTTGTC CTCTAGGATT TATTTCTGTT GTCCAAAAAA AAAANAAAAG AAAAGAAAAA      840
TTAAGGAGAA TTTTTGGTGT TAATGCTGAG GAATTGCTTG AGTGGTTAGT TGTTACCAAT      900
TTCTCTTTTG AACCTTTGGA GCTAAGGATG CTGAGTCTAG AGAAATGCTA GTCTCAAGCC      960
CTGTTAAGTC CCTCTGTTTC TAGCCCGTAG TTCATAGCAT CAGTGAACTG GAGCCACAAC     1020
AGCAAATTCT ATCAGCTGTG TACCATACAG CTTGTGCTGA AGGCGAATTT CTTGAGCCAT     1080
TACTCAGTAT AAAGCACTGA GTTCTATCTT TAGGATTTAT CTTTAAGAGC AAATTTCTGG     1140
TCAGCTGTGC TTCTGCAACC TAAAATATTT AAAGGGAGGT AGGTGTGGGC AGGAGGAGGA     1200
ATGATAAATT GGGCCAGGGC AAGAAAAATC TAGCTTCATA TAATTTGTCT GGGACTATAC     1260
ACCCTATATA ATGTTAGTTT TACAGAAGTA ATATGACTTT TGATTGCTAC ATACCACAAA     1320
GAGTTTATGA ACTGAGATCA TAAAGGGCAA CTGATGTGTG AAGAAAGTAG TCAGTACATC     1380
CTGGCTCATG CTCTGAAAGA ATATCCAGAG AGGCTCTCTC AAAGATCAGG GAGATGTATT     1440
CCCATGCCAT GCACCCTGCT TCCCAGCATT TCTGCATGGT CAAGTGAGCT TTATGCTCAT     1500
GAGCTTTAAG TATATAATTA TCCAGGATTT TAAATCCTCA ACTTGTTCTA GCTTGTGATC     1560
CCTCAAAGTT GGGTCATACG TTAGTGCTAG ATACTAGAAA TTTTCACTTT TCCACTGATC     1620
AGAGAGACAG ACATTAAAAA CAAAATAGA AGAAAGGAAA GCTTTCACCC TGCAGCTTCT      1680
TAGCAGGGAA CAATTGTCTT GCCAAAACTT TTTTCCCTTT TCTCTCCCAT TTTCTTTTAC     1740
CCAATCCCTT CTTACTCCTT GCCAGTGTGA CCATGCTTTC TTCTCTGTAG ATGTTAACAG     1800
TTAAGGCCTA TTTTCCTCGG GCACTTAACC AACCAATCAG AACACCACAT CTGTTAGGGG     1860
AGGTAACCTG GCCAACAGTG TATCCATCAC GTTAGCCCTG CTGGAGGGAA GGGACCCACA     1920
TTCACCTGCC CTCTGACCTG CCCCTTGATC CCATATCTAT TACCGTGTCC ATAGGAATAA     1980
TAGGTAAGGG CTCTGTCTCT GTCAAGCCAT GTAACAAGG ACACTGTTAA AAAAAAAAA      2040
AAGTCTGGCA TCAGAGGGAG CATGTGGAGA GCAACTTGGG AAGAACAAGT TCATTTTGTA     2100
TTGAATGATT TTTAATGAAT GCAATATTAA TCCTTGCAGA TGAGCAATAA TCATTAAAAT     2160
CGATTAAAAT GRTAAGRCCT TAAAAAAAAA AAANAAGGNN GAGAAGGANG GNNGGGGGTG     2220
NNGNGG                                                                2226
```

( 2 ) INFORMATION FOR SEQ ID NO:3:

( i ) SEQUENCE CHARACTERISTICS:
        ( A ) LENGTH: 504 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 969078

( x i ) SEQUENCE DESCRIPTION: SEQ ID NO:3:

```
Met  Ala  Lys  Met  Pro  Glu  Thr  Thr  Phe  Ala  Asp  Leu  Ser  Leu  Ala  Asp
 1                  5                   10                      15

Lys  Thr  Ala  Val  Lys  Lys  Ser  Ser  Ile  Glu  Ala  Arg  Arg  Phe  Ser  Asp
                20                  25                      30

Val  Ser  Thr  Cys  Ser  Phe  Ser  Ser  Thr  Cys  Phe  Thr  Gly  Ser  Ser  Asp
             35                  40                      45

Glu  Glu  Asp  Val  Ser  Pro  Lys  Asp  Asn  His  Gln  Arg  Asn  Ser  Ala  Gly
          50                  55                      60

Gly  Thr  Asp  Phe  Cys  Val  Lys  Ser  Ile  Ser  Lys  Ser  Ala  Phe  Gly  Arg
 65                  70                      75                      80
```

```
Arg Glu Ile Glu Ile Ala Glu Ser Glu Met Pro Gly Ile Met Thr Leu
                85                  90                  95

Arg Lys Arg Ala Lys Asp Glu Lys Pro Leu Lys Gly Ala Asn Ile Val
            100                 105                 110

Gly Cys Thr His Val Asn Ala Gln Ser Ala Val Leu Ile Glu Thr Leu
            115                 120                 125

Val Gln Leu Gly Ala Thr Val Arg Trp Ala Ala Cys Asn Ile Tyr Ser
        130                 135                 140

Thr Gln Asn Ala Val Ala Ala Ala Leu Ala Glu Ala Gly Ile Pro Ile
145                 150                 155                 160

Phe Ala Trp Arg Gly Glu Thr Glu Glu Glu Phe Trp Trp Cys Leu Asp
                165                 170                 175

Arg Ala Ile Tyr Ser Asp Gly Trp Gln Pro Asn Leu Ile Leu Asp Asp
            180                 185                 190

Gly Gly Asp Ala Thr His Leu Met Leu Lys Lys Tyr Pro Asp Tyr Phe
        195                 200                 205

Lys Ala Ile Arg Gly Ile Val Glu Glu Ser Val Thr Gly Val His Arg
    210                 215                 220

Leu Tyr Met Leu Ser Lys Gly Gly Lys Leu Thr Val Pro Ala Ile Asn
225                 230                 235                 240

Val Asn Asp Ser Val Thr Lys Asn Lys Phe Asp Thr Phe Tyr Thr Cys
                245                 250                 255

Arg Asp Ser Ile Leu Asp Ser Leu Lys Arg Thr Thr Asp Ile Met Phe
            260                 265                 270

Gly Gly Lys Gln Val Val Ile Cys Gly Tyr Gly Asp Val Gly Lys Gly
        275                 280                 285

Cys Ala Gln Ser Leu Lys Gly Gln Gly Cys Ile Val Tyr Val Thr Glu
290                 295                 300

Val Asp Pro Ile Cys Ala Leu Gln Ala Ala Met Asp Gly Phe Arg Val
305                 310                 315                 320

Val Arg Leu Asn Glu Val Ile Arg Thr Val Asp Val Val Val Thr Ala
                325                 330                 335

Thr Gly Asn Lys Asn Val Ile Thr Arg Asp His Met Asn Arg Met Lys
            340                 345                 350

Asn Gly Cys Ile Leu Cys Asn Met Gly His Ser Cys Ser Glu Ile Asp
        355                 360                 365

Val Asn Gly Leu His Thr Pro Glu Leu Thr Trp Glu Arg Val Arg Ser
    370                 375                 380

Gln Val Asp His Ile Arg Trp Pro Asp Gly Arg Met Ile Ile Leu Leu
385                 390                 395                 400

Ala Glu Gly Arg Leu Val Asn Leu Ser Cys Ser Thr Ile Ser Ser Phe
                405                 410                 415

Val Val Ser Val Ala Ser Ser Thr Gln Ala Leu Ala Leu Ile Glu Leu
            420                 425                 430

Phe Ser Ala Pro Gly Arg Tyr Lys Ser Asp Val Tyr Leu Leu Pro Lys
        435                 440                 445

Lys Met Asp Glu Tyr Val Ala Ser Leu His Leu Ala Thr Phe Asp Ala
    450                 455                 460

His Leu Thr Glu Leu Thr Asp Glu Gln Ser Lys Phe Met Gly Leu Asn
465                 470                 475                 480

Lys Ala Gly Pro Phe Lys Ala Asn Tyr Tyr Arg Leu Val Thr Leu Leu
                485                 490                 495

Ser Leu Ser Ile Leu His Ser Ser
            500
```

( 2 ) INFORMATION FOR SEQ ID NO:4:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 178277

( x i ) SEQUENCE DESCRIPTION: SEQ ID NO:4:

```
Met  Ser  Asp  Lys  Leu  Pro  Tyr  Lys  Val  Ala  Asp  Ile  Gly  Leu  Ala  Ala
  1              5                        10                       15

Trp  Gly  Arg  Lys  Ala  Leu  Asp  Ile  Ala  Glu  Asn  Glu  Met  Pro  Gly  Leu
               20                        25                       30

Met  Arg  Met  Arg  Glu  Arg  Tyr  Ser  Ala  Ser  Lys  Pro  Leu  Lys  Gly  Ala
               35                        40                       45

Arg  Ile  Ala  Gly  Cys  Leu  His  Met  Thr  Val  Glu  Thr  Ala  Val  Leu  Ile
          50                        55                       60

Glu  Thr  Leu  Val  Thr  Leu  Gly  Ala  Glu  Val  Gln  Trp  Ser  Ser  Cys  Asn
 65                        70                       75                       80

Ile  Phe  Ser  Thr  Gln  Asn  His  Ala  Ala  Ala  Ala  Ile  Ala  Lys  Ala  Gly
                    85                        90                       95

Ile  Pro  Val  Tyr  Ala  Trp  Lys  Gly  Glu  Thr  Asp  Glu  Glu  Tyr  Leu  Trp
                   100                       105                      110

Cys  Ile  Glu  Gln  Thr  Leu  Tyr  Phe  Lys  Asp  Gly  Pro  Leu  Asn  Met  Ile
               115                       120                      125

Leu  Asp  Asp  Gly  Gly  Asp  Leu  Thr  Asn  Leu  Ile  His  Thr  Lys  Tyr  Pro
     130                       135                      140

Gln  Leu  Leu  Pro  Gly  Ile  Arg  Gly  Ile  Ser  Glu  Glu  Thr  Thr  Thr  Gly
145                       150                       155                      160

Val  His  Asn  Leu  Tyr  Lys  Met  Met  Ala  Asn  Gly  Ile  Leu  Lys  Val  Pro
                    165                       170                      175

Ala  Ile  Asn  Val  Asn  Asp  Ser  Val  Thr  Lys  Ser  Lys  Phe  Asp  Asn  Leu
               180                       185                      190

Tyr  Gly  Cys  Arg  Glu  Ser  Leu  Ile  Asp  Gly  Ile  Lys  Arg  Ala  Thr  Asp
               195                       200                      205

Val  Met  Ile  Ala  Gly  Lys  Val  Ala  Val  Val  Ala  Gly  Tyr  Gly  Asp  Val
     210                       215                      220

Gly  Lys  Gly  Cys  Ala  Gln  Ala  Leu  Arg  Gly  Phe  Gly  Ala  Arg  Val  Ile
225                       230                       235                      240

Ile  Thr  Glu  Ile  Asp  Pro  Ile  Asn  Ala  Leu  Gln  Ala  Ala  Met  Glu  Gly
                    245                       250                      255

Tyr  Glu  Val  Thr  Thr  Met  Asp  Glu  Ala  Cys  Gln  Glu  Gly  Asn  Ile  Phe
               260                       265                      270

Val  Thr  Thr  Thr  Gly  Cys  Ile  Asp  Ile  Ile  Leu  Gly  Arg  His  Phe  Glu
          275                       280                      285

Gln  Met  Lys  Asp  Asp  Ala  Ile  Val  Cys  Asn  Ile  Gly  His  Phe  Asp  Val
     290                       295                      300

Glu  Ile  Asp  Val  Lys  Trp  Leu  Asn  Glu  Asn  Ala  Val  Glu  Lys  Val  Asn
305                       310                       315                      320

Ile  Lys  Pro  Gln  Val  Asp  Arg  Tyr  Arg  Leu  Lys  Asn  Gly  Arg  Arg  Ile
                    325                       330                      335
```

-continued

| Ile | Leu | Leu | Ala | Glu | Gly | Arg | Leu | Val | Asn | Leu | Gly | Cys | Ala | Met | Gly |
| | | | 340 | | | | 345 | | | | | | 350 | | |

| His | Pro | Ser | Phe | Val | Met | Ser | Asn | Ser | Phe | Thr | Asn | Gln | Val | Met | Ala |
| | | 355 | | | | | 360 | | | | | 365 | | | |

| Gln | Ile | Glu | Leu | Trp | Thr | His | Pro | Asp | Lys | Tyr | Pro | Val | Gly | Val | His |
| | 370 | | | | | | 375 | | | | | 380 | | | |

| Phe | Leu | Pro | Lys | Lys | Leu | Asp | Glu | Ala | Val | Ala | Glu | Ala | His | Leu | Gly |
| 385 | | | | | | 390 | | | | | 395 | | | | 400 |

| Lys | Leu | Asn | Val | Lys | Leu | Thr | Lys | Leu | Thr | Glu | Lys | Gln | Ala | Gln | Tyr |
| | | | | 405 | | | | | 410 | | | | | 415 | |

| Leu | Gly | Met | Ser | Cys | Asp | Gly | Pro | Phe | Lys | Pro | Asp | His | Tyr | Arg | Tyr |
| | | | 420 | | | | | 425 | | | | | 430 | | |

( 2 ) INFORMATION FOR SEQ ID NO:5:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 904132

( x i ) SEQUENCE DESCRIPTION: SEQ ID NO:5:

| Met | Ser | Asp | Lys | Leu | Pro | Tyr | Lys | Val | Ala | Asp | Ile | Gly | Leu | Ala | Ala |
| 1 | | | | 5 | | | | | 10 | | | | | 15 | |

| Trp | Gly | Arg | Lys | Ala | Leu | Asp | Ile | Ala | Glu | Asn | Glu | Met | Pro | Gly | Leu |
| | | | 20 | | | | | 25 | | | | | 30 | | |

| Met | Arg | Met | Arg | Glu | Met | Tyr | Ser | Ala | Ser | Lys | Pro | Leu | Lys | Gly | Ala |
| | | | 35 | | | | | 40 | | | | | 45 | | |

| Arg | Ile | Ala | Gly | Cys | Leu | His | Met | Thr | Val | Glu | Thr | Ala | Val | Leu | Ile |
| | 50 | | | | | 55 | | | | | 60 | | | | |

| Glu | Thr | Leu | Val | Ala | Leu | Gly | Ala | Glu | Val | Arg | Trp | Ser | Ser | Cys | Asn |
| 65 | | | | | 70 | | | | | 75 | | | | | 80 |

| Ile | Phe | Ser | Thr | Gln | Asp | His | Ala | Ala | Ala | Ile | Ala | Lys | Ala | Gly | |
| | | | | 85 | | | | | 90 | | | | | 95 | |

| Ile | Pro | Val | Phe | Ala | Trp | Lys | Gly | Glu | Thr | Asp | Glu | Glu | Tyr | Leu | Trp |
| | | | | 100 | | | | | 105 | | | | | 110 | |

| Cys | Ile | Glu | Gln | Thr | Leu | His | Phe | Lys | Asp | Gly | Pro | Leu | Asn | Met | Ile |
| | | | 115 | | | | | 120 | | | | | 125 | | |

| Leu | Asp | Asp | Gly | Gly | Asp | Leu | Thr | Asn | Leu | Ile | His | Thr | Lys | Tyr | Pro |
| | 130 | | | | | 135 | | | | | 140 | | | | |

| Gln | Leu | Leu | Ser | Gly | Ile | Arg | Gly | Ile | Ser | Glu | Glu | Thr | Thr | Thr | Gly |
| 145 | | | | | 150 | | | | | 155 | | | | | 160 |

| Val | His | Asn | Leu | Tyr | Lys | Met | Met | Ser | Asn | Gly | Ile | Leu | Asn | Val | Pro |
| | | | | 165 | | | | | 170 | | | | | 175 | |

| Ala | Ile | Asn | Val | Asn | Asp | Ser | Val | Thr | Lys | Ser | Lys | Phe | Asp | Asn | Leu |
| | | | 180 | | | | | 185 | | | | | 190 | | |

| Tyr | Gly | Cys | Arg | Glu | Ser | Leu | Ile | Asp | Gly | Ile | Lys | Arg | Ala | Thr | Asp |
| | | 195 | | | | | 200 | | | | | 205 | | | |

| Val | Met | Ile | Ala | Gly | Lys | Val | Ala | Val | Ala | Gly | Tyr | Gly | Asp | Val |
| | 210 | | | | | 215 | | | | | 220 | | | | |

| Gly | Lys | Gly | Cys | Ala | Gln | Ala | Leu | Arg | Gly | Phe | Gly | Ala | Arg | Val | Ile |
| 225 | | | | | 230 | | | | | 235 | | | | | 240 |

| Ile | Thr | Glu | Ile | Asp | Pro | Ile | Asn | Ala | Leu | Gln | Ala | Ala | Met | Glu | Gly |
| | | | | 245 | | | | | 250 | | | | | 255 | |

| | | | | | | | | | | | | | | |
|---|---|---|---|---|---|---|---|---|---|---|---|---|---|---|
|Tyr|Glu|Val|Thr 260|Thr|Met|Asp|Glu|Ala 265|Cys|Lys|Glu|Gly|Asn 270|Ile|Phe|
|Val|Thr|Thr 275|Thr|Gly|Cys|Val|Asp 280|Ile|Ile|Leu|Gly|Arg 285|His|Phe|Glu|
|Gln|Met 290|Lys|Asp|Asp|Ala|Ile 295|Val|Cys|Asn|Ile|Gly 300|His|Phe|Asp|Val|
|Glu 305|Ile|Asp|Val|Lys|Trp 310|Leu|Asn|Glu|Asn|Ala 315|Val|Glu|Lys|Val|Asn 320|
|Ile|Lys|Pro|Gln|Val 325|Asp|Arg|Tyr|Trp|Leu 330|Lys|Asn|Gly|Arg|Arg 335|Ile|
|Ile|Leu|Leu|Ala 340|Glu|Gly|Arg|Leu|Val 345|Asn|Leu|Gly|Cys|Ala 350|Met|Gly|
|His|Pro|Ser 355|Phe|Val|Met|Ser|Asn 360|Ser|Phe|Thr|Asn|Gln 365|Val|Met|Ala|
|Gln|Ile 370|Glu|Leu|Trp|Thr|His 375|Pro|Asp|Lys|Tyr|Pro 380|Val|Gly|Val|His|
|Phe 385|Leu|Pro|Lys|Lys|Leu 390|Asp|Glu|Ala|Val|Ala 395|Glu|Ala|His|Leu|Gly 400|
|Lys|Leu|Asn|Val|Lys 405|Leu|Thr|Lys|Leu|Thr 410|Glu|Lys|Gln|Ala|Gln 415|Tyr|
|Leu|Gly|Met|Pro 420|Ile|Asn|Gly|Pro|Phe 425|Lys|Pro|Asp|His|Tyr 430|Arg|Tyr|

POLYNUCLEOTIDES ENCODING HUMAN S-ADENOSYL-5-HOMOCYSTEINE HYDROLASE DERIVED FROM BLADDER

FIELD OF THE INVENTION

This invention relates to nucleic acid and amino acid sequences of a human S-adenosyl-5-homocysteine hydrolase and to the use of these sequences in the diagnosis, prevention, and treatment of infection, neoplastic disorders, and disorders of the immune system.

BACKGROUND OF THE INVENTION

Covalent modification of cellular substrates with methyl groups has been implicated in the pathology of disease and cancer (Goldberg, D. M. and Diamandis, E. P. (1993) Clin. Chem. 39:2360–2374; Gloria, L. et al. (1996) Cancer 78:2300–2306). Cytosine hypermethylation of eukaryotic DNA prevents transcriptional activation of a gene (Turker, M. S. and Bestor, T. H. (1997) Mutat. Res. 386:119–130). Maturation of 45S precursor RNA to yield 28S and 18S rRNA in mammalian cells requires methylation of a 2'-hydroxyl group of a ribose unit followed by cleavage, whereas bacterial rRNA maturation requires methylation of the nucleotide base (Stryer, L. (1981) *Biochemistry*, W. H. Freeman and Company, San Francisco, Calif. p612). Hypermethylated viral DNA is transcribed at higher rates than hypo- or hemimethylated DNA in infected cells (Willis, D. B. et al. (1989) Cell. Biophys. 15:97–111).

S-adenosylmethionine is an important source of methyl groups for methylation reactions in the cell (Bottiglieri, T. and Hyland, K. (1994) Acta Neurol. Scand. Suppl.154:19–26). Methyltransferase activity catalyzes the transfer of methyl groups from S-adenosylmethionine to acceptor molecules such as phosphotidylethanolamine or the polynucleotide 5' cap of viral mRNA (Stryer, L. (supra) p 494; Montgomery, J. A. et al. (1982) J. Med. Chem. 25:626–629). The residual product of this reaction is S-adenosyl-5-homocysteine (AdoHcy). Elevated levels of AdoHcy in the cell downregulate methyltransferase activity and elevate intracellular levels of L-methionine, but decreasing intracellular AdoHcy levels allows further methyltransferase reactions to continue (Newsholme, E. A. and Leech, A. R. (1983) *Biochemistry for the Medical Sciences*, John Wiley and Sons, Chichester, U. K. p436).

S-adenosyl-5-homocysteine hydrolase (SAHH; EC 3.3.1.1) catalyzes the reversible hydrolysis of AdoHcy to adenosine and L-homocysteine in the presence of tightly-bound NAD$^+$ (Palmer, J. L. and Abeles, R. H. (1979) J. Biol. Chem. 254:1217–1226). SAHH has been identified in man, in mouse, and as a variant in adult Drosophila (Coulter-Karis, D. E. and Hershfield, M. S. (1989) Ann. Hum. Genet. 53:169–175; Bethin, K. E. et al. (1995) J. Biol. Chem. 270:20698–20702; Martin, C. H. et al. (1995) Proc. Natl. Acad. Sci. 92:8398–8402). There is evidence that fly SAHH also functions as a trans-regulatory homeoprotein during embryonic development (DeLorenzi, M. et al. (1988) EMBO J. 7:3223–3231). In addition, the 76 residue N-terminal domain of fly SAHH has sequence homology with human and murine nuclear proteins (Inagaki, H. et al. (1996) J. Biol. Chem. 271:12525–12531; Harada, Y. N. et al. (1995) Genomics 28:59–65).

SAHH has been identified as a target for antiviral, anticancer and anti-inflammatory drug design in its role as a rate-limiting step in methyltransferase reactions that use S-adenosylmethionine as substrate [Montgomery, J. A. et al. (supra); Wnuk, S. F. et al. (1994) J. Med Chem. 37:3579–3587; Gloria, L. et al. (supra)]. Unsaturated and carboxylic nucleoside analogues act as antitumor or antiviral agents in vitro and inhibit SAHH in patients with chronic lymphocytic leukaemias (Phadtare, S. et al. (1991) J. Med. Chem. 34:421–429; Warzoch, K. (1997) Eur. J. Cancer 33:170–173).

The discovery of a new human S-adenosyl-5homocysteine hydrolase and the polynucleotides encoding it satisfies a need in the art by providing new compositions which are useful in the diagnosis, prevention and treatment of infection, neoplastic disorders and disorders of the immune system.

SUMMARY OF THE INVENTION

The invention features a substantially purified polypeptide, human S-adenosyl-5homocysteine hydrolase (SAHH), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding SAHH under conditions suitable for the expression of the polypeptide; and b) recovering the polypeptide from the host cell culture.

The invention also provides a pharmaceutical composition comprising a substantially purified SAHH having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which specifically binds to the polypeptide comprising the amino acid sequence of SEQ ID NO:1.

Still further, the invention provides a purified agonist which modulates the activity of the polypeptide of SEQ ID NO:1.

The invention also provides a method for treating or preventing infection comprising administering to a subject in need of such treatment an effective amount of antagonist to SAHH.

The invention also provides a method for treating or preventing neoplastic disorders comprising administering to a subject in need of such treatment an effective amount of antagonist to SAHH.

The invention also provides a method for treating or preventing disorders of the immune system comprising administering to a subject in need of such treatment an effective amount of antagonist to SAHH.

The invention also provides a method for detecting a polynucleotide which encodes SAHH in a biological sample comprising the steps of: a) hybridizing a polynucleotide sequence complementary to the polynucleotide sequence encoding SAHH (SEQ ID NO:1) to nucleic acid material of a biological sample, thereby forming a hybridization complex; and b) detecting the hybridization complex, wherein the presence of the complex correlates with the presence of a polynucleotide encoding SAHH in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C, 1D, 1E, 1F, 1G, 1H, and 1I show the amino acid sequence (SEQ ID NO:1) and nucleic acid sequence (SEQ ID NO:2) of SAHH. The alignment was produced using MACDNASIS PRO software (Hitachi Software Engineering Co. Ltd. San Bruno, Calif.).

Figure 2A:
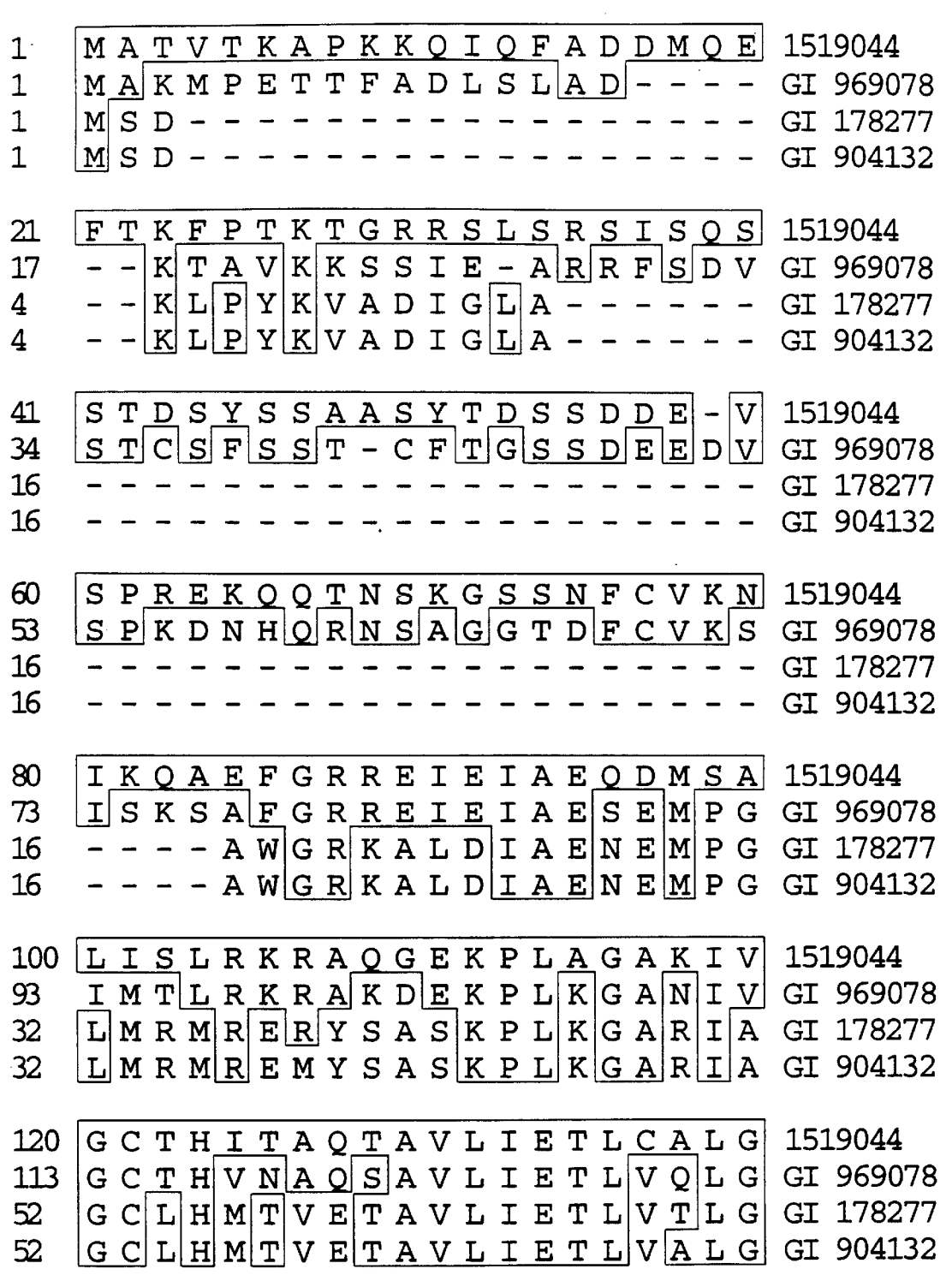
Figure 2B:
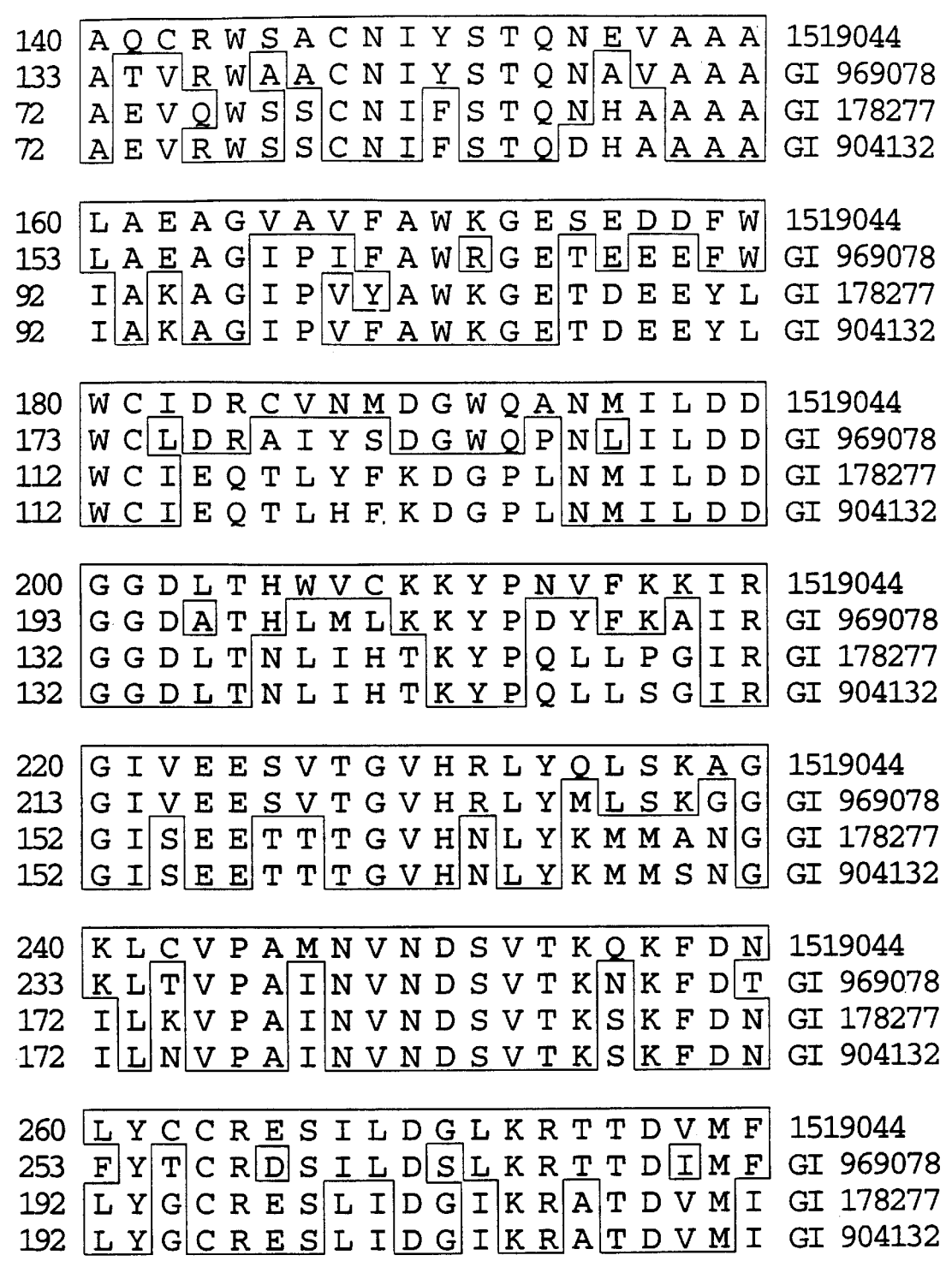
Figure 2D:
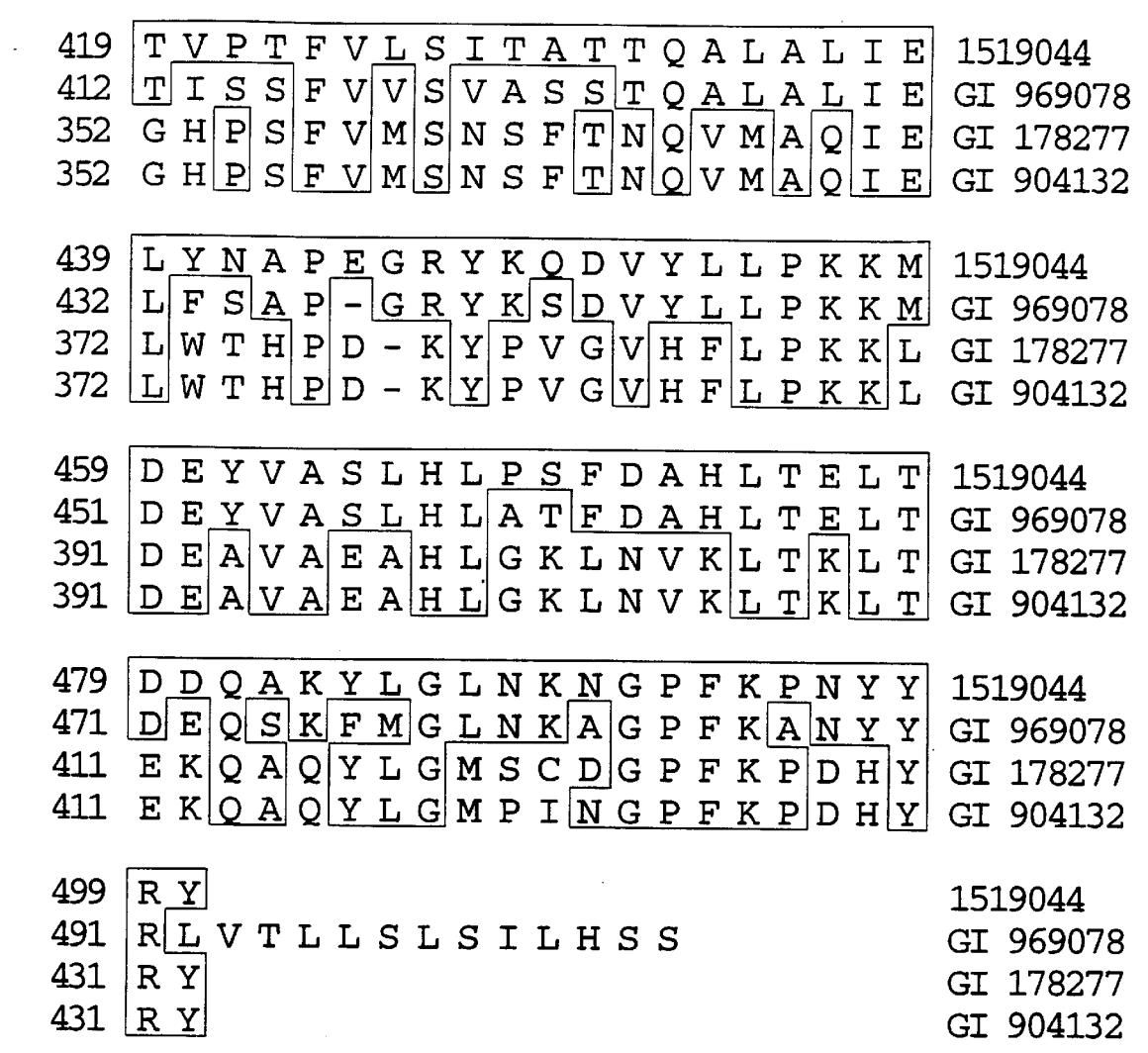

FIGS. 2A, 2B, 2C, and 2D show the amino acid sequence alignments among SAHH (1519044; SEQ ID NO:1), Drosophila SAHH (GI 969078; SEQ ID NO:3), human SAHH (GI 178277; SEQ ID NO:4), and murine SAHH (GI 904132; SEQ ID NO:5), produced using the multisequence alignment program of DNASTAR software (DNASTAR Inc, Madison Wis.).

DESCRIPTION OF THE INVENTION

Figure 3:
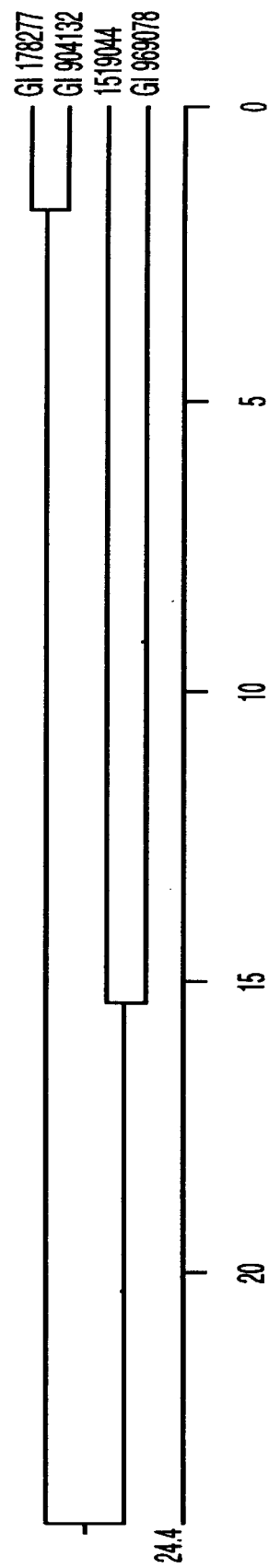
FIG. 3 shows the phylogenic relationship between SAHH, Drosophila SAHH (GI 969078; SEQ ID NO:3), human SAHH (GI 178277; SEQ ID NO:4), and murine SAHH (GI 904132; SEQ ID NO:5), produced using the multisequence alignment program of DNASTAR software (DNASTAR Inc, Madison Wis.). The X-axis represents genetic distance.

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

SAHH, as used herein, refers to the amino acid sequences of substantially purified SAHH obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to SAHH, increases or prolongs the duration of the effect of SAHH. Agonists may include proteins, nucleic acids, carbohydrates, or any other molecules which bind to and modulate the effect of SAHH.

An "allele" or "allelic sequence", as used herein, is an alternative form of the gene encoding SAHH. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding SAHH as used herein include those with deletions, insertions, or substitutions of different nucleotides resulting in a polynucleotide that encodes the same or a functionally equivalent SAHH. Included within this definition are polymorphisms which may or may not be readily detectable using a particular oligonucleotide probe of the polynucleotide encoding SAHH, and improper or unexpected hybridization to alleles, with a locus other than the normal chromosomal locus for the polynucleotide sequence encoding SAHH. The encoded protein may also be "altered" and contain deletions, insertions, or substitutions of amino acid residues which produce a silent change and result in a functionally equivalent SAHH. Deliberate amino acid substitutions may be made on the basis of similarity in polarity, charge, solubility, hydrophobicity, hydrophilicity, and/or the amphipathic nature of the residues as long as the biological or immunological activity of SAHH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of SAHH are preferably about 5 to about 15 amino acids in length and retain the biological activity or the immunological activity of SAHH. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to SAHH, decreases the amount or the duration of the effect of the biological or immunological activity of SAHH. Antagonists may include proteins, nucleic acids, carbohydrates, or any other molecules which decrease the effect of SAHH.

As used herein, the term "antibody" refers to intact molecules as well as fragments thereof, such as Fa, F(ab')$_2$, and Fv, which are capable of binding the epitopic determinant. Antibodies that bind SAHH polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic SAHH, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein refers broadly to any composition containing the given polynucleotide sequence. The composition may comprise a dry formulation or an aqueous solution. Compositions comprising polynucleotide sequences encoding SAHH (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence .

The term "correlates with expression of a polynucleotide", as used herein, indicates that the detection of the presence of ribonucleic acid that is similar to SEQ ID NO:2 by northern analysis is indicative of the presence of mRNA encoding SAHH in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to SAHH or the encoded SAHH. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0 t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of SAHH. For example, modulation may cause an increase or a decrease in protein activity, binding characteristics, or any other biological, functional or immunological properties of SAHH.

"Nucleic acid sequence", as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers", "primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length SAHH and fragments thereof.

The term "sample", as used herein, is used in its broadest sense. A biological sample suspected of containing nucleic acid encoding SAHH, or fragments thereof, or SAHH itself may comprise a bodily fluid, extract from a cell, chromosome, organelle, or membrane isolated from a cell, a cell, genomic DNA, RNA, or cDNA (in solution or bound to a solid support), a tissue, a tissue print, and the like.

The terms "specific binding" or "specifically binding", as used herein, refer to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of SAHH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human S-adenosyl-5-homocysteine hydrolase (hereinafter referred to as "SAHH"), the polynucleotides encoding SAHH, and the use of these compositions for the diagnosis, prevention, or treatment of infection, neoplastic disorders and disorders of the immune system.

Nucleic acids encoding the SAHH of the present invention were first identified in Incyte Clone 1519044 from the tumor bladder cDNA library (BLADTUT04) using a computer search for amino acid sequence alignments. A consensus sequence, SEQ ID NO:2, was derived from the following overlapping and/or extended nucleic acid sequences: Incyte Clones 1519044 (BLADTUT04), 1615782 (BRAITUT12), 1656951 (URETTUT01), 1729453 (BRSTTUT08), 2552596 (LUNGTUT06), 1226352 (COLNNOT01), 475708 (MMLR2DT01), 1427878 (SINTBST01), 2621771 (KERANOT02), 2097340 (BRAITUT02), and 1471038 (LUNGTUT03).

In one embodiment, the invention encompasses a polypeptide comprising the amino acid sequence of SEQ ID NO:1, as shown in FIGS. 1A, 1B, 1C, 1D, 1E, 1F, 1G, 1H, and 1I. SAHH is 500 amino acids in length and has a potential $NAD^+$ binding site between V-292 and C-296, two potential N-glycosylation sites at N-249 and N-414, one protein kinase A phosphorylation site at T-272, twelve potential casein kinase II phosphorylation sites at S-40, S-50, S-54, S-55, S-60, T-152, S-174, S-266, T-310, S-370, T-372, and S-391, protein kinase C phosphorylation sites at T-28, S-60, S-102, and S-378, and one potential tyrosine kinase phosphorylation site at Y-261. As shown in FIGS. 2A, 2B, 2C, and 2D, SAHH has chemical and structural homology with Drosophila SAHH (GI 969078; SEQ ID NO:3), with human SAHH (GI 178277; SEQ ID NO:4), and with murine SAHH (GI 904132; SEQ ID NO:5). In particular, SAHH and Drosophila SAHH share 90% identity, a potential $NAD^+$ binding site, both potential N-glycosylation sites, nine of the potential casein kinase II phosphorylation sites, two of the potential protein kinase C phosphorylation sites, the potential tyrosine kinase phosphorylation site, and a similar 76 residue N-terminal domain. SAHH shares 51% identity with human SAHH, a potential $NAD^+$ binding site, both potential N-glycosylation sites, four of the potential casein kinase II phosphorylation sites, and the potential tyrosine kinase phosphorylation site. FIG. 3 shows that SAHH is genetically more closely related to Drosophila SAHH and that human and murine SAHH are proteins distinct from SAHH and Drosophila SAHH. Northern analysis shows the expression of this sequence in various libraries, at least 34% of which are immortalized or cancerous, in particular tumors of the brain, lung, ovary, breast, pancreas, and of the blood; and at least 59% of which involve the immune response. Of particular note is the expression of SAHH in tissue inflammation, disorders of the gut, and disorders of secretory tissue.

The invention also encompasses SAHH variants. A preferred SAHH variant is one having at least 80%, and more preferably at least 90%, amino acid sequence identity to the SAHH amino acid sequence (SEQ ID NO:1) and which retains at least one biological or other functional characteristics of SAHH. A most preferred SAHH variant is one having at least 95% amino acid sequence identity to SEQ ID NO:1.

The invention also encompasses polynucleotides which encode SAHH. Accordingly, any nucleic acid sequence which encodes the amino acid sequence of SAHH can be used to produce recombinant molecules which express SAHH. In a particular embodiment, the invention encompasses the polynucleotide comprising the nucleic acid sequence of SEQ ID NO:2 as shown in FIGS. 1A, 1B, 1C, 1D, 1E, 1F, 1G, 1H, and 1I.

It will be appreciated by those skilled in the art that as a result of the degeneracy of the genetic code, a multitude of nucleotide sequences encoding SAHH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring SAHH, and all such variations are to be considered as being specifically disclosed.

Although nucleotide sequences which encode SAHH and its variants are preferably capable of hybridizing to the nucleotide sequence of the naturally occurring SAHH under appropriately selected conditions of stringency, it may be advantageous to produce nucleotide sequences encoding SAHH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding SAHH and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode SAHH and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding SAHH or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding SAHH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In is particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial 30 chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode SAHH may be used in recombinant DNA molecules to direct expression of SAHH, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express SAHH.

As will be understood by those of skill in the art, it may be advantageous to produce SAHH-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter SAHH encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding SAHH may be ligated to a heterologous sequence to encode a fusion protein. For example, to screen peptide libraries for inhibitors of SAHH activity, it may be useful to encode a chimeric SAHH protein that can be recognized by a commercially available antibody. A fusion protein may also be engineered to contain a cleavage site located between the SAHH encoding sequence and the heterologous protein sequence, so that SAHH may be cleaved and purified away from the heterologous moiety.

In another embodiment, sequences encoding SAHH may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of SAHH, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of SAHH, or any part thereof, may be altered during direct synthesis and/or combined using chemical methods with sequences from other proteins, or any part thereof, to produce a variant polypeptide.

In order to express a biologically active SAHH, the nucleotide sequences encoding SAHH or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding SAHH and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding SAHH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding SAHH, vectors based on SV40 or EBV may be used with an appropriate selectable marker.

In bacterial systems, a number of expression vectors may be selected depending upon the use intended for SAHH. For example, when large quantities of SAHH are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding SAHH may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomvces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding SAHH may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1 984) EMBO J. 3:1671–1680; Broglie, R. et al. (1984) Science 224:838–843; and Winter, J. et al. (1991) Results Probi. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express SAHH. For example, in one such system, *Autographa californica* nuclear polyhedrosis virus (AcNPV) is used as a vector to express foreign genes in *Spodoptera frugiperda* cells or in Trichoplusia larvae. The sequences encoding SAHH may be cloned into a non-essential region of the virus, such as the polyhedrin gene, and placed under control of the polyhedrin promoter. Successful insertion of SAHH will render the polyhedrin gene inactive and produce recombinant virus lacking coat protein. The recombinant viruses may then be used to infect, for example, *S. frugiperda* cells or Trichoplusia larvae in which SAHH may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding SAHH may be ligated into an adenovirus transcription/translation complex consisting of the late promoter and tripartite leader sequence. Insertion in a non-essential E1 or E3 region of the viral genome may be used to obtain a viable virus which is capable of expressing SAHH in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding SAHH. Such signals include the ATG initiation codon and adjacent sequences. In cases where sequences encoding SAHH, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express SAHH may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding SAHH is inserted within a marker gene sequence, transformed cells containing sequences encoding SAHH can be identified by the absence of marker gene function. Alternatively, a marker gene can be placed in tandem with a sequence encoding SAHH under the control of a single promoter. Expression of the marker gene in response to induction or selection usually indicates expression of the tandem gene as well.

Alternatively, host cells which contain the nucleic acid sequence encoding SAHH and express SAHH may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding SAHH can be detected by DNA—DNA or DNA-RNA hybridization or amplification using probes or fragments or fragments of polynucleotides encoding SAHH. Nucleic acid amplification based assays involve the use of oligonucleotides or oligomers based on the sequences encoding SAHH to detect transformants containing DNA or RNA encoding SAHH.

A variety of protocols for detecting and measuring the expression of SAHH, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on SAHH is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding SAHH include oligolabeling, nick translation, end-labeling or PCR amplification using a labeled nucleotide. Alternatively, the sequences encoding SAHH, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding SAHH may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode SAHH may be designed to contain signal sequences which direct secretion of SAHH through a prokaryotic or eukaryotic cell membrane. Other constructions may be used to join sequences encoding SAHH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and SAHH may be used to facilitate purification. One such expression vector provides for expression of a fusion protein containing SAHH and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying SAHH from the fusion protein. A discussion of vectors which contain fusion proteins is provided in Kroll, D. J. et al. (1993; DNA Cell Biol. 12:441–453).

In addition to recombinant production, fragments of SAHH may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of SAHH may be chemically synthesized separately and combined using chemical methods to produce the full length molecule.

THERAPEUTICS

Chemical and structural homology exits among SAHH and SAHH from Drosophila (GI 969078), man (GI 178277), and mouse (GI 904132). In addition, SAHH is expressed in brain, gut, lung, circulatory tissue, kidney, uterus, breast, prostate, thyroid, skin, liver and spleen; secretory and fetal tissue. Therefore, SAHH appears to play a role in infection, neoplastic disorders, and disorders of the immune system, disorders in which SAHH is overexpressed.

Therefore, in one embodiment, an antagonist of SAHH may be administered to a subject to prevent or treat infection. Infection may include, but is not limited to, viral [adenoviruses (ARD, pneumonia), arenaviruses (lymphocytic choriomeningitis), bunyaviruses (Hantavirus), coronaviruses (pneumonia, chronic bronchitis), hepadnaviruses (hepatitis), herpesviruses (HSV, VZV, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackie-virus), polyomaviruses (BK virus, JC virus), poxviruses (smallpox), reovirus (Colorado tick fever), retroviruses (HIV, HTLV), rhabdoviruses (rabies), rotaviruses (gastroenteritis), and togaviruses (encephalitis, rubella)], bacterial, fungal, parasitic, protozoal, or helminthic infections. In one aspect, antibodies which specifically bind SAHH may be used directly as an antagonist or indirectly as a targeting or delivery mechanism for bringing a pharmaceutical agent to cells or tissue which express SAHH.

In another embodiment, a vector expressing the complement of the polynucleotide encoding SAHH may be administered to a subject to treat or prevent infection including, but not limited to, the types of infection described above.

In another embodiment, an antagonist of SAHH may be administered to a subject to prevent or treat neoplastic disorders. Neoplastic disorders may include, but are not limited to adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind SAHH may be used directly as an antagonist or indirectly as a targeting or delivery mechanism for bringing a pharmaceutical agent to cells or tissue which express SAHH.

In another embodiment, a vector expressing the complement of the polynucleotide encoding SAHH may be administered to a subject to treat or prevent neoplastic disorders including, but not limited to, the types of neoplastic disorders described above.

In another embodiment, an antagonist of SAHH may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, extracorporeal circulation; and trauma. In one aspect, antibodies which specifically bind SAHH may be used directly as an antagonist or indirectly as a targeting or delivery mechanism for bringing a pharmaceutical agent to cells or tissue which express SAHH.

In another embodiment, a vector expressing the complement of the polynucleotide encoding SAHH may be administered to a subject to treat or prevent an immune disorder including, but not limited to, those described above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of SAHH may be produced using methods which are generally known in the art. In particular, purified SAHH may be used to produce antibodies or to screen libraries of pharmaceutical agents to identify those which specifically bind SAHH.

Antibodies to SAHH may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with SAHH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to SAHH have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of SAHH amino acids may be fused with those of another protein such as keyhole limpet hemocyanin and antibody produced against the chimeric molecule.

Monoclonal antibodies to SAHH may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454).

Alternatively, techniques described for the production of single chain antibodies may be adapted, using methods known in the art, to produce SAHH-specific single chain antibodies. Antibodies with related specificity, but of distinct idiotypic composition, may be generated by chain shuffling from random combinatorial IMMUNOGLOBIN libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for SAHH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between SAHH and its specific antibody. A two-site, monoclonal-based immunoassay utilizing monoclonal antibodies reactive to two non-interfering SAHH epitopes is preferred, but a competitive binding assay may also be employed (Maddox, supra).

In another embodiment of the invention, the polynucleotides encoding SAHH, or any fragment or complement thereof, may be used for therapeutic purposes. In one aspect, the complement of the polynucleotide encoding SAHH may be used in situations in which it would be desirable to block the transcription of the mRNA. In particular, cells may be transformed with sequences complementary to polynucleotides encoding SAHH. Thus, complementary molecules or fragments may be used to modulate SAHH activity, or to achieve regulation of gene function. Such technology is now well known in the art, and sense or antisense oligonucleotides or larger fragments, can be designed from various locations along the coding or control regions of sequences encoding SAHH.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding SAHH. These techniques are described both in Sambrook et al. (supra) and in Ausubel et al. (supra).

Genes encoding SAHH can be turned off by transforming a cell or tissue with expression vectors which express high levels of a polynucleotide or fragment thereof which encodes SAHH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding SAHH (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding SAHH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding SAHH. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of SAHH, antibodies to SAHH, mimetics, agonists, antagonists, or inhibitors of SAHH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmnaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0. 1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of SAHH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example SAHH or fragments thereof, antibodies of SAHH, agonists, antagonists or inhibitors of SAHH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind SAHH may be used for the diagnosis of conditions or diseases characterized by expression of SAHH, or in assays to monitor patients being treated with SAHH, agonists, antagonists or inhibitors. The antibodies useful for diagnostic purposes may be prepared in the same manner as those described above for therapeutics. Diagnostic assays for SAHH include methods which utilize the antibody and a label to detect SAHH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring SAHH are known in the art and provide a basis for diagnosing altered or abnormal levels of SAHH expression. Normal or standard values for SAHH expression are established by combining body fluids or cell extracts taken from normal mammalian subjects, preferably human, with antibody to SAHH under conditions suitable for complex formation The amount of standard complex formation may be quantified by various methods, but preferably by photometric means. Quantities of SAHH expressed in subject samples, control and disease, from biopsied tissues are compared with the standard values. Deviation between standard and subject values establishes the parameters for diagnosing disease.

In another embodiment of the invention, the polynucleotides encoding SAHH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of SAHH may be correlated with disease. The diagnostic assay may be used to distinguish between absence, presence, and excess expression of SAHH, and to monitor regulation of SAHH levels during therapeutic intervention.

In one aspect, hybridization with PCR probes which are capable of detecting polynucleotide sequences, including genomic sequences, encoding SAHH or closely related molecules, may be used to identify nucleic acid sequences which encode SAHH. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding SAHH, alleles, or related sequences.

Probes may also be used for the detection of related sequences, and should preferably contain at least 50% of the nucleotides from any of the SAHH encoding sequences. The hybridization probes of the subject invention may be DNA or RNA and derived from the nucleotide sequence of SEQ ID NO:2 or from genomic sequence including promoter, enhancer elements, and introns of the naturally occurring SAHH.

Means for producing specific hybridization probes for DNAs encoding SAHH include the cloning of nucleic acid sequences encoding SAHH or SAHH derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding SAHH may be used for the diagnosis of conditions, disorders, or diseases which are associated with expression of SAHH. Examples of such conditions or diseases include may include, but is not limited to, viral [adenoviruses (ARD, pneumonia), arenaviruses (lymphocytic choriomeningitis), bunyaviruses (Hantavirus), coronaviruses (pneumonia, chronic bronchitis), hepadnaviruses (hepatitis), herpesviruses (HSV, VZV, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackie-virus), polyomaviruses (BK virus, JC virus), poxviruses (smallpox), reovirus (Colorado tick fever), retroviruses (HIV, HTLV), rhabdoviruses (rabies), rotaviruses (gastroenteritis), and togaviruses (encephalitis, rubella)], bacterial, fungal, parasitic, protozoal, or helminthic infections; adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, extracorporeal circulation; and trauma. The polynucleotide sequences encoding SAHH may be used in Southern or northern analysis, dot blot, or other membrane-based technologies; in PCR technologies; or in dipstick, pin, ELISA assays or microarrays utilizing fluids or tissues from patient biopsies to detect altered SAHH expression. Such qualitative or quantitative methods are well known in the art.

In a particular aspect, the nucleotide sequences encoding SAHH may be useful in assays that detect activation or induction of various cancers, particularly those mentioned above. The nucleotide sequences encoding SAHH may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding SAHH in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of SAHH, a normal or standard profile for expression is established. This may be accomplished by combining body fluids or cell extracts taken from normal subjects, either animal or human, with a sequence, or a fragment thereof, which encodes SAHH, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding SAHH may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of SAHH include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides derived from any of the polynucleotide sequences described herein may be used as targets in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devices (slot blot or dot blot apparatus), materials (any suitable solid support), and machines (including robotic instruments) and may contain 8, 24, 96, 384, 1536 or 6144 oligonucleotides, or any other number between two and one million which lends itself to the efficient use of commercially available instrumentation.

In order to conduct sample analysis using the microarrays, the RNA or DNA from a biological sample is made into hybridization probes. The mRNA is isolated, and CDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode SAHH may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding SAHH on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11 q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, SAHH, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between SAHH and the agent being tested, may be measured.

Another technique for drug screening which may be used provides for high throughput screening of compounds having suitable binding affinity to the protein of interest as described in published PCT application WO84/03564. In this method, as applied to SAHH large numbers of different small test compounds are synthesized on a solid substrate, such as plastic pins or some other surface. The test compounds are reacted with SAHH, or fragments thereof, and washed. Bound SAHH is then detected by methods well known in the art. Purified SAHH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding SAHH specifically compete with a test compound for binding SAHH. In this manner, the antibodies can be used to detect the presence of any peptide which shares one or more antigenic determinants with SAHH.

In additional embodiments, the nucleotide sequences which encode SAHH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BLADTUT04 cDNA Library Construction

The BLADTUT04 CDNA library was constructed from cancerous bladder tissue from a 60-year-old Caucasian male following excision during a radical cystectomy of a grade 3 of 3 transitional cell carcinoma in the left bladder wall which extended through the muscularis propria into the perivascular fat. Family history included diabetes, type I, in both the mother and father, a malignant neoplasm of the stomach for the father, and atherosclerosis in a sibling.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCl cushion using a Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen OLIGOTEX kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Cat. #18248–013; GiBco BRL, Gaithersburg, Md.).

The commercial plasmid PSPORT1 (GiBco BRL) was digested with EcoRI restriction enzyme (New England Biolabs, Beverley, Mass.). The overhanging ends of the plasmid were filled in using Klenow enzyme (New England Biolabs) and 2'-deoxynucleotide 5'-triphosphates (dNTPs). The plasmid was self-ligated and transformed into the bacterial host, *E. coli* strain JM109. An intermediate plasmid produced by the bacteria failed to digest with EcoRI confirming the desired loss of the EcoRI restriction site.

This intermediate plasmid (PSPORT1-ΔRI) was then digested with Hind III restriction enzyme (New England Biolabs) and the overhang was filled in with Klenow and dNTPs. A 10-mer linker of sequence 5'. . . CGGAATTCCG . . . 3' was phosphorylated and ligated onto the blunt ends. The product of the ligation reaction was digested with EcoRI and self-ligated. Following transformation into JM109 host cells, plasmids were isolated and screened for the digestibility with EcoRI but not with Hind III. A single colony which met this criteria was designated pINCY 1. The plasmid produced by this colony was sequenced and found to contain several copies of the 10-mer linker. These extra linkers did not present a problem as they were eliminated when the vector was prepared for cloning.

The plasmid was tested for its ability to incorporate cDNAs from a library prepared using Not I and EcoR I restriction enzymes. Several clones were sequenced and a single clone containing an insert of approximately 0.8 kb was selected to prepare a large quantity of the plasmid for library production. After digestion with Not I and EcoR I, the plasmid and the CDNA insert were isolated on an agarose gel and the vector was purified on a QIAQUICK (QIAGEN, Chatsworth, Calif.) column for use in library construction.

cDNAs were fractionated on a SEPHAROSE CL4B column (Cat. #275105-01; Pharmacia), and those cDNAs exceeding 400 bp were ligated into pINCY vector (Incyte). The plasmid pINCY was subsequently transformed into DH5α™ competent cells (Cat. #18258-012; GIBco BPL).

II Isolation and Sequencing of CDNA Clones

Plasmid DNA was released from the cells and purified using the REAL Prep 96 Plasmid Kit (Catalog #26173; QIAGEN, Inc., Chatsworth, Calif.). The recommended protocol was employed except for the following changes: 1) the bacteria were cultured in 1 ml of sterile Terrific Broth (Catalog #22711, GIBCO BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from M J Research, Watertown, Mass.) and Applied Biosystems 377 DNA Sequencing Systems; and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a Glxxx±p (where xxx is pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score wehich is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding SAHH occurs. Abundance and percent abundance are also reported. Abundance directly reflects the number of times a particular transcript is represented in a CDNA library, and percent abundance is abundance divided by the total number of sequences examined in the cDNA library.

V Extension of SAHH Encoding Polynucleotides

The nucleic acid sequence of the Incyte Clone 1519044 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the CDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer—primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Kienow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, NH). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25 1 16, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the SAHH-encoding sequence, or any part thereof, is used to decrease or inhibit expression of naturally occurring SAHH. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of SAHH, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the SAHH-encoding transcript.

IX Expression of SAHH

Expression of SAHH is accomplished by subcloning the cDNAs into appropriate vectors and transforming the vectors into host cells. In this case, the cloning vector is also used to express SAHH in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of SAHH into the bacterial growth media which can be used directly in the following assay for activity.

X Demonstration of SAHH Activity

Human S-adenosyl-5homocysteine hydrolase (SAHH) is assayed in the synthesis direction at 25° C. in 25 mM MOPS buffer, pH 7.5, containing 5 mM homocysteine and 10 $\mu$M [$^3$H]adenosine (0.3 mCi/ml) in a total volume of 50 $\mu$l (Hohman, R. J. et al. (1984) Arch. Biochem. Biophys. 233:785–795). The samples are incubated for 10 or 20 minutes, and the reaction terminated by addition of 15 $\mu$l of a stop mixture containing 13% trichloroacetic acid, 7 mM adenosine, and 7 mM AdoHcy to serve as markers on TLC plates. After centrifugation to remove precipitated proteins, 5 $\mu$l of supernatant are spotted on PEI-Cellulose F-coated plastic TLC sheets, which have been developed in n-butanol:ethanol:$H_2O$ (2:1:1). AdoHcy and adenosine are visualized under UV light, and the spots cut out and counted in liquid scintillant.

SAHH may be assayed in the hydrolysis direction by spectrophotometry (Hohman, R. J. and Veron, M. (1984) FEBS Lett. 165:265–268). The assay mixture contains 975 $\mu$l buffer (25 mM MOPS (pH 7.5), 20 mM NaCl), 182 $\mu$l 4.7 mM AdoHcy, and 2 $\mu$l adenosine deaminase (Sigma Chem Co, St. Louis, Mo, cat. # A-9626, 2250 units/ml). 50 $\mu$l assay mixture is added to 850 $\mu$l buffer, and the reaction started by addition of purified SAHH (5–10 $\mu$l). The conversion of AdoHcy to inosine, via adenosine, is followed at 265 nm, where the change in the extinction coefficient is $-7.6 \times 10^3$ $M^{-1}.cm^{-1}$. One unit of SAHH will hydrolyze 1 nmole AdoHcy/min at 25° C.

XI Production of SAHH Specific Antibodies

SAHH that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring SAHH Using Specific Antibodies

Naturally occurring or recombinant SAHH is substantially purified by immunoaffinity chromatography using antibodies specific for SAHH. An immunoaffinity column is constructed by covalently coupling SAHH antibody to an activated chromatographic resin, such as CNBr-activated SEPHAROSE (Pharmacia & Upjohn). After the coupling, the resin is blocked and washed according to the manufacturer's instructions.

Media containing SAHH is passed over the immunoaffinity column, and the column is washed under conditions that allow the preferential absorbance of SAHH (e.g., high ionic strength buffers in the presence of detergent). The column is eluted under conditions that disrupt antibody/SAHH binding (eg, a buffer of pH 2–3 or a high concentration of a chaotrope, such as urea or thiocyanate ion), and SAHH is collected.

XIII Identification of Molecules Which Interact with SAHH

SAHH or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled SAHH, washed and any wells with labeled SAHH complex are assayed. Data obtained using different concentrations of SAHH are used to calculate values for the number, affinity, and association of SAHH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding human S-adenosyl-5-homocysteine hydrolase comprising the amino acid sequence of SEQ ID NO:1 or fragments of SEQ ID NO:1 having hydrolase activity.

2. A composition comprising the polynucleotide sequence of claim 1.

3. A polynucleotide sequence which hybridizes under the stringent conditions of 40° C. and wash conditions of 0.1× saline sodium citrate and 0.5% sodium dodecyl sulfate to the polynucleotide sequence of claim 1.

4. A polynucleotide sequence which is complementary to the polynucleotide sequence of claim 1.

5. An isolated and purified polynucleotide sequence comprising SEQ ID NO:2.

6. A composition comprising the polynucleotide sequence of claim 5.

7. A polynucleotide sequence which is complementary to the polynucleotide sequence of claim 5.

8. An expression vector containing the polynucleotide sequence of claim 1.

9. A host cell containing the vector of claim 8.

10. A method for producing a polypeptide comprising the amino acid sequence of SEQ ID NO:1, or fragments of SEQ ID NO:1 having hydrolase activity, the method comprising the steps of:

a) culturing the host cell of claim 10 under conditions suitable for the expression of the polypeptide; and b) recovering the polypeptide from the host cell culture.

* * * * *

UNITED STATES PATENT AND TRADEMARK OFFICE
CERTIFICATE OF CORRECTION

PATENT NO. : 5,854,023
DATED : December 29, 1998
INVENTOR(S) : Hillman et al.

It is certified that error appears in the above-identified patent and that said Letters Patent is hereby corrected as shown below:

Col. 50, line 43, delete "claim 10 under" and insert --claim 9 under--.

Signed and Sealed this

First Day of February, 2000

Attest:

Attesting Officer

Q. TODD DICKINSON

Acting Commissioner of Patents and Trademarks